United States Patent [19]

Badorc et al.

[11] Patent Number: 5,607,952

[45] Date of Patent: Mar. 4, 1997

[54] SUBSTITUTED 4-PHENYLTHIAZOLE DERIVATIVES, PROCESS FOR THEIR PREPARATION AND PHARMACEUTICAL COMPOSITIONS CONTAINING THEM

[75] Inventors: Alain Badorc, Roquettes; Marie-Françoise Bordes, Labarthe sur Leze; Paul de Cointet, Toulouse; Jean-Marc Herbert, Tournefeuille; Jean-Pierre Maffrand, Portet/Garonne, all of France

[73] Assignee: Sanofi, Paris, France

[21] Appl. No.: 577,097

[22] Filed: Dec. 22, 1995

[30] Foreign Application Priority Data

Dec. 28, 1994 [FR] France .................. 94 15805

[51] Int. Cl.$^6$ .................. A61K 31/445; C07D 211/60
[52] U.S. Cl. .................. 514/326; 514/318; 546/194; 546/209
[58] Field of Search .................. 514/318, 326; 546/194, 209

[56] References Cited

U.S. PATENT DOCUMENTS 5,405,848  4/1995  Sanfillipo et al. .................. 514/258

FOREIGN PATENT DOCUMENTS 542363    5/1993  European Pat. Off. .
0542363   5/1993  United Kingdom .
WO91/09857 7/1991 WIPO .

*Primary Examiner*—C. Warren Ivy
*Assistant Examiner*—Garth M. Dahlen
*Attorney, Agent, or Firm*—Jacobson, Price, Holman & Stern, PLLC

[57] ABSTRACT

The invention concerns compounds of formula

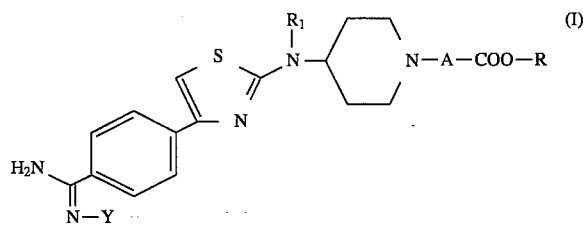

in which R, A, $R_1$ and Y are as defined in claim 1. The instant compounds have an affinity for the fibrinogen receptor: the complex of the glycoproteins IIb/IIIa (GP IIb/IIIa); more particularly, the subject of the present invention is new inhibitors of platelet aggregation which are antagonists of the GP IIb/IIIa receptors, of nonpeptide structure, which are active via the parenteral and oral routes.

16 Claims, No Drawings

SUBSTITUTED 4-PHENYLTHIAZOLE DERIVATIVES, PROCESS FOR THEIR PREPARATION AND PHARMACEUTICAL COMPOSITIONS CONTAINING THEM

The invention concerns compounds of formula

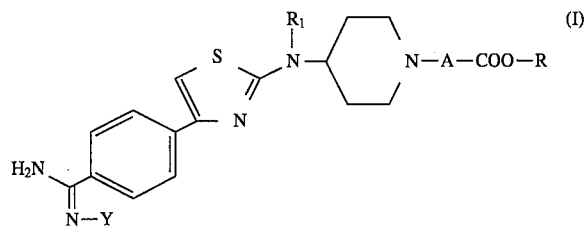

in which R, A, $R_1$ and Y are as defined in claim 1.

The present invention relates to new derivatives of 2-amino-4-phenylthiazole as well as their salts, the process for preparing them and the pharmaceutical compositions containing them.

The compounds of the present invention differ from other 1,3-thiazole derivatives in their original structure and in their unexpected pharmacological properties. Indeed, the compounds of the invention have an affinity for the fibrinogen receptor: the complex of the glycoproteins IIb/IIIa (GP IIb/IIIa); more particularly, the subject of the present invention is new inhibitors of platelet aggregation which are antagonists of the GP IIb/IIIa receptors, of nonpeptide structure, which are active via the parenteral and oral routes.

Platelet activation and aggregation are associated with pathological states such as disorders of the cardiovascular and cerebrovascular system such as one found in thromboembolic disorders associated with atherosclerosis and with diabetes such as unstable angina, cerebral attack, restenosis following angioplasty, endarterectomy or fitting of stents, with rethrombosis following thrombolysis, with infarction, with dementia of ischaemic origin, with peripheral arterial diseases, with haemodialysis, with auricular fibrillations or alternatively during the use of vascular protheses, of aorto-coronary by-pass, but also with osteoporosis, with cancer and with metastasis or with glomerulonephritis.

The contribution of the platelets to these pathological processes is due to their capacity to form platelet aggregates or clots, in particular on the atherial walls damaged following rupture of the atheromatous plaque.

Platelets are known to play an essential role in the maintenance of haemostasis and in the pathogeneses of arterial thrombosis. It has been demonstrated that the activation of the platelets increases during coronary thrombolysis which can affect reperfusion and lead to reocclusion of the artery.

Clinical studies carried out with aspirin and ticlopidine demonstrated that the inhibition of platelet aggregation was an effective means of preventing cardiovascular accidents in several types of populations at risk.

The platelets are activated by a large number of agonists, the consequence of which is the modification of their shape, as well as the modification of the secretion of the granular contents and the aggregation. The aggregation of the platelets then contributes to the formation of clots.

Several endogenous agonists such as adenosine-5-diphosphate (ADP), serotonin, arachidonic acid, platelet activation factor (PAF), adrenaline, thrombin or collagen have been identified.

Given the simultaneous involvement of several endogenous agonists in the activation of the aggregation and of the platelet functions, an inhibitor which would act against all the agonists would represent an antiplatelet agent which is more effective than the currently available medicinal products which are products acting specifically against a particular agonist.

The platelet aggregation inhibitors currently available are active against only one type of agonist. This is the case of aspirin, which is active against arachidonic acid, of ticlopidine which is active against ADP, of the inhibitors of thromboxane $A_2$ synthetase or of the antagonists of the thromboxane $A_2$ receptor or alternatively of hirudin which acts against thrombin.

Recently, a mode of action common to all the known agonists was identified. It is the activation of the membrane complex of the glycoproteins GP IIb/IIIa which then binds circulating fibrinogen, thus bringing about the bridging between several platelets and therefore the platelet aggregation. Recent reviews have shown the value of products which are antagonists of GP IIb/IIIa, for example Drugs of the Future, 1994, 19 (2), 135–159; or 19 (5), 461–476 or alternatively 19 (8), 757–764.

The GP IIb/IIIa of nonstimulated platelets does not bind to soluble proteins. On the other hand, the GP IIb/IIIa of activated platelets is known to bind to adhesive proteins such as fibrinogen, von Willebrand's factor, fibronectin, or vitronectin. The binding of fibrinogen and of the yon Willebrand's factor to GP IIb/IIIa causes platelet aggregation. The binding of fibrinogen is partly mediated by the recognition sequence Arg-Gly-Asp (RGD) which is common to the adhesive proteins which bind to GP IIb/IIIa (Thromb. Res. 1993, 72, 231–245).

Antagonists of GP IIb/IIIa have already been the subject of patent applications; this is the case for example of EP-608858, EP-542363, EP-539343, EP-478363, EP-623595, WO 93/14077, WO 94/22910 and during the past few years, the antithrombotic properties of inhibitors of GP IIb/IIIa have been described (see Drugs of the Future cited above). Among the compounds studied, a monoclonal antibody c7E3 (Abciximab) exhibited advantageous antithrombotic properties in human clinical medicine which are described especially in N. Engl., J. Med., 1994, 330, 956–61. These results are of particular interest since they show that such products are good candidates in the prevention of thrombosis and its complications. This product requires administration via the intravenous route. However, among the inhibitors of GP IIb/IIIa studied up until now in man, some appear to exhibit activity via the oral route.

This is especially the case for compounds such as SC 54684, L 703-014, GR 144053, DMP 728, or alternatively BIBU-104 (Zablocki, J.A. et al., Exp. Opin. Invest. Drugs., 1994, 3, 5, 449–55).

The development of antagonists of GP IIb/IIIa which are active via the oral route therefore constitutes a promising new approach for the therapy of pathologies dependent on platelet aggregation.

There is a need today which consists in being able to have a platelet aggregation inhibitor specific for GP IIb/IIIa which would inhibit the activation and the aggregation of platelets regardless of the agonist involved; it should be active via the oral route.

Such an inhibitor would be endowed with therapeutic properties against platelet aggregation which are more effective than those of the specific antagonists currently available.

Thus, the present invention relates to the derivatives of thiazole which are useful as antagonists of the complex of the glycoproteins GP IIb/IIIa, to the pharmaceutical compositions containing them, to the use of these compounds alone or in combination with other antithrombotic agents such as anticoagulants and/or thrombolytic agents, for the treatments of thromboembolic disorders and of any pathologies which are dependent on them.

The present invention also relates to combinations of active ingredient which are pharmaceutical compositions containing at least one compound according to the invention, with anticoagulants such as warfarin, heparin, boropeptides, hirudins or argatroban or platelet aggregation inhibitors such as aspirin, ticlopidine or alternatively thrombolytic agents such as plasminogen tissue activator, anistreplase, urokinase or streptokinase or combinations thereof, the compositions comprising these mixtures being used to inhibit platelet aggregation and thromboembolic disorders.

The compounds of the present invention correspond to the following formula:

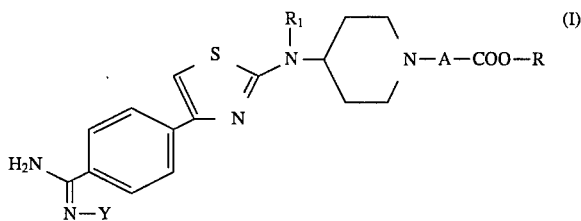

in which $R_1$ represents hydrogen, a $C_1$–$C_5$ alkyl, a $C_3$–$C_8$ cycloalkyl, an aralkyl whose alkyl part has from 1 to 5 carbon atoms, an alkoxycarbonylalkyl group or an (alkoxycarbonylaryl)-alkyl group in which the alkoxy and alkyl parts have from 1 to 3 carbon atoms; a carboxyalkyl group or a (carboxyaryl)alkyl group in which the alkyl part has from 1 to 3 carbon atoms;

A represents either (i) a methylene group optionally mono- or disubstituted by a $C_1$–$C_5$ alkyl group, by an alkoxycarbonyl group whose alkoxy part has from 1 to 5 carbon atoms, by an alkoxycarbonylalkyl group in which the alkoxy and alkyl parts have from 1 to 5 carbon atoms, by a carboxyalkyl group whose alkyl part has from 1 to 5 carbon atoms, by a group chosen from phenyl and benzyl which are unsubstituted or substituted on the aromatic ring by $C_1$–$C_5$ alkyl, $C_1$–$C_5$ alkoxy, hydroxyl, halogen or trifluoromethyl, by a pyridyl group, or (ii) an ethylene group;

R represents hydrogen, a $C_1$–$C_5$ alkyl group, an aryl group or an aralkyl group whose alkyl part has from 1 to 5 carbon atoms, the said aryl and aralkyl groups being unsubstituted or substituted on the aromatic ring by hydroxyl, $C_1$–$C_3$ alkoxy, $C_1$–$C_3$ alkanoyloxy, halogen, trifluoromethyl or $C_1$–$C_5$ alkyl;

Y represents hydrogen, a —$COOR_2$ group in which $R_2$ represents a $C_1$–$C_5$ alkyl group; an aryl group or an aralkyl group whose alkyl part has from 1 to 5 carbon atoms, it being possible for the said aryl and aralkyl groups to be optionally substituted on the aromatic ring by $C_1$–$C_5$ alkyl; or a —$COR_3$ group in which $R_3$ represents $C_1$–$C_5$ alkyl;

or one of their salts.

According to the invention, aryl is understood to mean especially an aromatic ring, for example a $C_6$–$C_{10}$ aromatic ring especially phenyl, 1-naphthyl or 2-naphthyl.

Likewise, the aryl part of the aralkyl, (alkoxycarbonylaryl)alkyl and (carboxyaryl) alkyl groups according to the invention preferably represents an aromatic ring, for example a $C_6$–$C_{10}$ aromatic ring, especially phenyl, 1-naphthyl or 2-naphthyl.

The salts of the compounds of formula (I) according to the present invention comprise those obtained with inorganic or organic acids which allow appropriate separation or crystallization of the compounds of formula (I), such as picric acid or oxalic acid or an optically active acid, for example a mandelic or camphosulphonic acid, and the pharmaceutically acceptable salts such as the hydrochloride, hydrobromide, sulphate, acetate, hydrogen sulphate, dihydrogen phosphate, methanesulphonate, methyl sulphate, maleate, fumarate, sulphonate, 2-naphthalenesulphonate, glycolate, gluconate, citrate, isethionate, benzoate, salicylate, ascorbate, tartrate, succinate, lactate, glutarate, toluenesulphonate, ascorbate or alternatively the salts of inorganic bases in the form of alkali metal salts such as for example sodium salts.

The present invention also relates to the optical isomers of the compounds of formula (I) which optionally contain a chiral centre, as well as their salts.

The enantiomers and the racemic mixtures of the compounds of formula (I) are therefore an integral part of the invention.

In the present description, the alkyl groups or the alkoxy groups are straight or branched. The alkyl groups are for example methyl, ethyl, n-propyl, i-propyl, n-butyl, sec-butyl or t-butyl and the alkoxy groups are for example methoxy, ethoxy, n,.propoxy, i-propoxy, n-butoxy, sec-butoxy or t-butoxy.

The compounds of formula (I) in which R represents methyl or ethyl are preferred.

Another group of preferred compounds consists of those of formula:

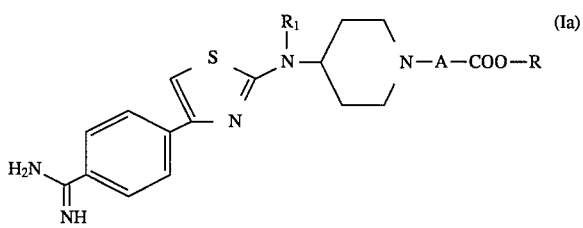

in which —A— represents an optionally monosubstituted methylene group, $R_1$ represents hydrogen, a methyl group, a carboxyalkyl group or an alkoxycarbonylalkyl group and —COO—R is as defined for (I), or one of their salts.

Another group of preferred compounds consists of the compounds of formula:

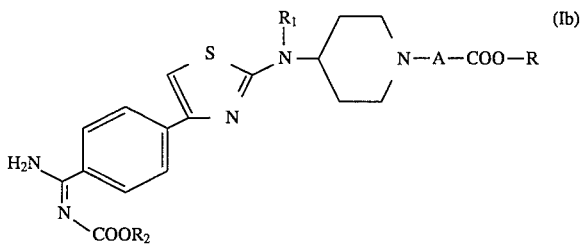

in which —A— represents an optionally monosubstituted methylene group and COO—R, $R_1$ and $R_2$ are as defined for (I), or one of their salts.

Particularly preferred is the group of compounds of formula:

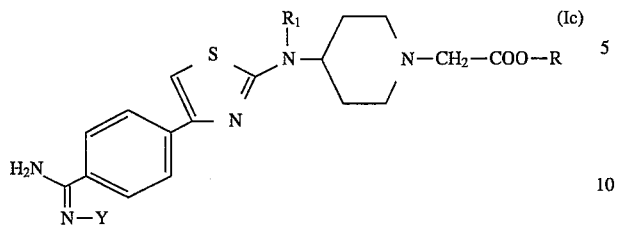

(Ic)

in which R, Y and $R_1$ are as defined for (I) or one of their salts.

More particularly preferred is the group of compounds of formula:

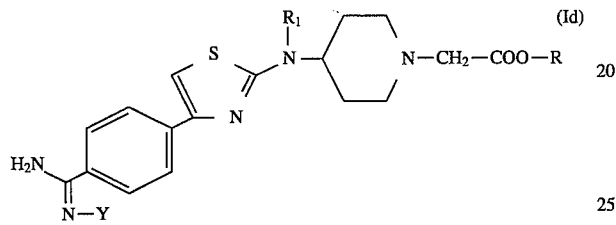

(Id)

in which $R_1$ represents hydrogen, a carboxyalkyl group or an alkoxycarbonylalkyl group, R represents hydrogen, a methyl or ethyl group and Y is as defined for (I) or one of their salts.

The compounds more particularly preferred are:

a) methyl (4-{4-[4-(aminoiminomethyl)phenyl]1,3-thiazol-2-ylamino}piperid-1yl)acetate, b) (4-{4-[4-(aminoiminomethyl)phenyl]-1,3-thiazol-2-yl-amino}piperid-1-yl}acetic acid, c) methyl (4-{4-[4-(amino(N-ethoxycarbonylimino)m-ethyl)-phenyl]-1,3-thiazol-2-ylamino}piperid-1-yl)acetate, d) ethyl (4-{4-[4-(aminoiminomethyl)phenyl]-1,3-thiazol-2-ylamino}-piperid-1-yl)acetate, e) ethyl (4-{4-[4-(amino(N-ethoxycarbonylimino)m-ethyl)-phenyl]-1,3-thiazol-2ylamino}piperid-1-yl)acetate, f) (4-{4-[4-(aminoiminomethyl)phenyl]-1,3-thiazol-2-yl-N-carboxymethylamino}piperid-1-yl)acetic acid, g) ethyl 3-[N-{4-[4-(aminoiminomethyl)phenyl]-1,3-thiazol-2-yl}-N-(1-ethoxycarbonylmethylpiperid-4-yl)-amino]propionate, h) 3-[N-{4-[4-(aminoiminomethyl)phenyl]-1,3-thiazol-2-yl}-N-(1-carboxymethylpiperid-4-yl)amino]propionic acid, i) ethyl 3-[N-{4-[4-(aminoethoxycarbonyliminomethyl)-phenyl]-1,3-thiazol-2-yl}-N-(1-ethoxycarbonylmethyl-piperid-4-yl)amino]propionate, or one of their salts.

The present invention also relates to a process for the preparation of the compounds (I) from the intermediate compounds of formula (II).

This process comprises the steps consisting of:

(a) deprotecting the cyclic amine functional group of a compound of formula (II):

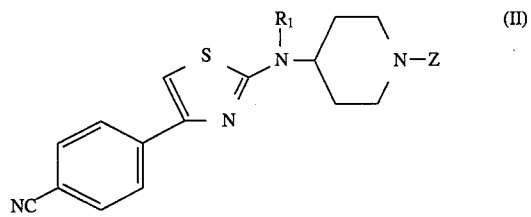

(II)

in which $R_1$ is as defined for (I) and Z represents an amine-protecting group such as a benzyl, so as to obtain a free amine of formula (III):

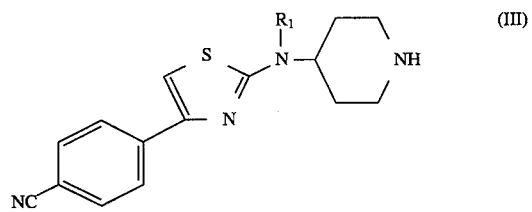

(III)

in which $R_1$ is as defined for (I);

when Z represents a benzyl, the deprotection can be carried out by the action of chloroformates;

(b) N-alkylating the resulting compound of formula (III)
  (i) either by a reaction with a halogenated derivative of formula:

$$X-A-COO-R \qquad (1)$$

in which X represents a leaving group such as a tosyl group or a halogen, preferably chlorine or bromine, and A and R are as defined for (I), in a solvent chosen for example from alkanols or dimethylformamide in the presence of an alkaline agent such as an alkali metal carbonate or triethylamine;

(ii) or, by Michael reaction with an α, β-unsaturated ester of formula $$CH_2=CH-COOR \qquad (2)$$

or $$RCOO-CH=CH-COOR \qquad (3)$$

in an alkanol where R is as defined for (I), in order to obtain a compound of formula:

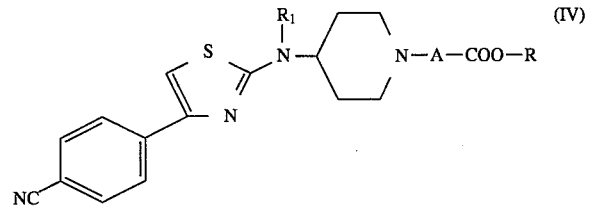

(IV)

in which A, R and $R_1$ are as defined for (I), (c) subjecting the resulting compound to the Pinner reaction by reacting the nitrile (IV) in an acidic medium in an alkanol in order to obtain the imidate salt with which an amine, for example ammonia, is then reacted in order to obtain the amidine of formula:

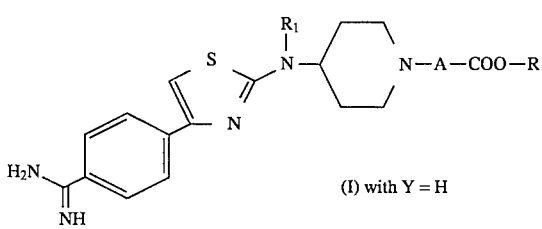

(I) with Y = H in which A, R and $R_1$ are as defined for (I), the compound obtained representing a compound of formula (I) in which Y is hydrogen, (d) where appropriate, reacting the amidine obtained in step (c),
(i) either with a chloroformate of formula:

$Cl-COO-R_2$ in which $R_2$ is as defined for (I), in a solvent such as dimethylformamide in an alkaline medium, for example in the presence of triethylamine or an alkali metal carbonate, in order to obtain the compound of formula

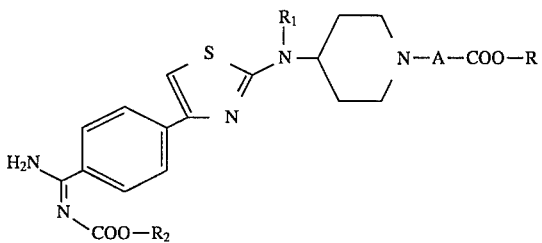

representing a compound of formula (I) in which Y represents $-COO-R_2$ and $R_1$, $R_2$, A and R are as defined for (I);

(ii) or with an acylating agent such as $Cl-CO-R_3$ in which $R_3$ is as defined for (I) in order to obtain a compound of formula (I) in which Y represents $-CO-R_3$, $R_1$, A and R being as defined for (I);

(e) where appropriate, hydrolysing the corresponding ester precursor obtained in step (c), for example in an acidic medium in the presence of hydrochloric acid, in order to obtain a compound of formula (I) in which R is hydrogen, or one of their salts.

The intermediate compounds of formula (II) in which $R_1$ is different from hydrogen can be prepared simply from the corresponding compounds of formula (II) in which $R_1$ is a hydrogen atom, by the action of a derivative of formula $R_1 X$ in which $R_1$ is as defined for (I) and X is a leaving group such as an alkylsulphonyloxy or arylsulphonyloxy group or a halogen atom, in the presence either of a strong base such as an alkali metal hydride, for example sodium hydride, or such as potassium tert-butoxide in an anhydrous solvent such as dimethylformamide or tetrahydrofuran, or by solid-liquid phase transfer catalysis (PTC) in the presence of a phase transfer catalyst, for example tetrabutylammonium bromide, and a base such as potassium carbonate, in an inert solvent such as toluene.

In the case where $R_1 = -CH_2-CH_2-COOR_4$ (with $R_4$ representing a hydrogen or a $C_1-C_2$ alkyl group), the compounds of formula (II) in which $R_1 = -CH_2-CH_2-COOR_4$ can be advantageously obtained from the corresponding compounds of formula (II) in which $R_1$ is a hydrogen atom, by a Michael type reaction with an α,β-unsaturated compound of formula $CH_2=CH-COOR_4$ ($R_4$ representing a hydrogen atom or a $C_1-C_2$ alkyl group), under solid-liquid PTC conditions in the presence of a catalyst such as tetrabutylammonium bromide and a base such as potassium carbonate, in an inert solvent such as toluene.

The intermediate compounds (II) in which $R_1$ represents hydrogen are prepared according to methods well known to a person skilled in the art and especially according to the Hantzsch method, Comprehensive Heterocyclic Chemistry, A. Katritzky, 1984, Vol 6, from starting materials which are commercially available or which are prepared according to known methods.

The compounds of formula (II), (III) and (IV) and their salts are novel compounds which constitute another aspect of the invention.

They can be represented by the following formula (v):

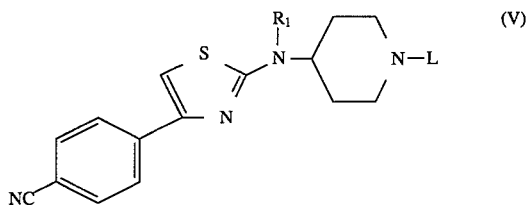

in which $R_1$ is as defined above and L represents hydrogen, a group Z or a group $-A-COOR$, Z, A and R being as defined above.

The above compounds of formula (I) also comprise those in which one or more hydrogen, carbon or halogen atoms, especially chlorine or fluorine, have been replaced with their radioactive isotope, for example tritium or $^{14}$Carbon. Such labelled compounds are useful in research, metabolism or pharmacokinetic work, in biochemical assays as receptor ligand.

The following SCHEME 1 presents all the reactions discussed above:

SCHEME 1

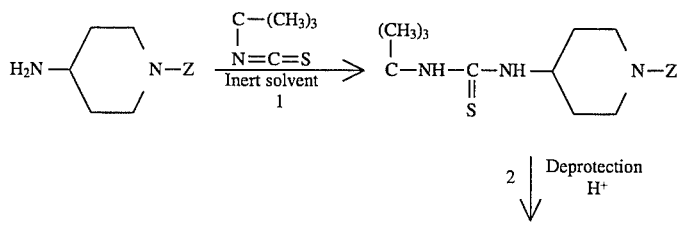

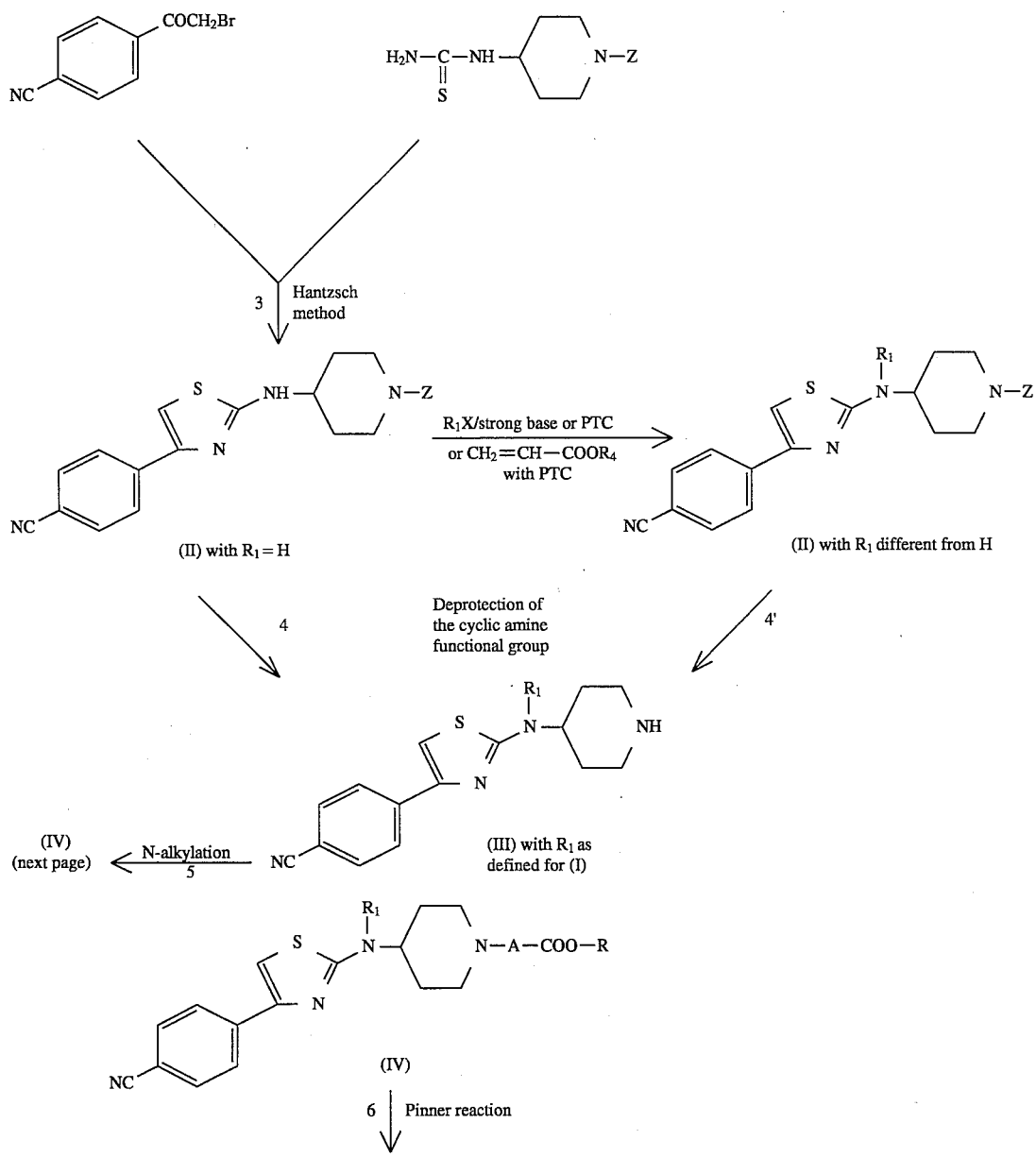

-continued
SCHEME 1

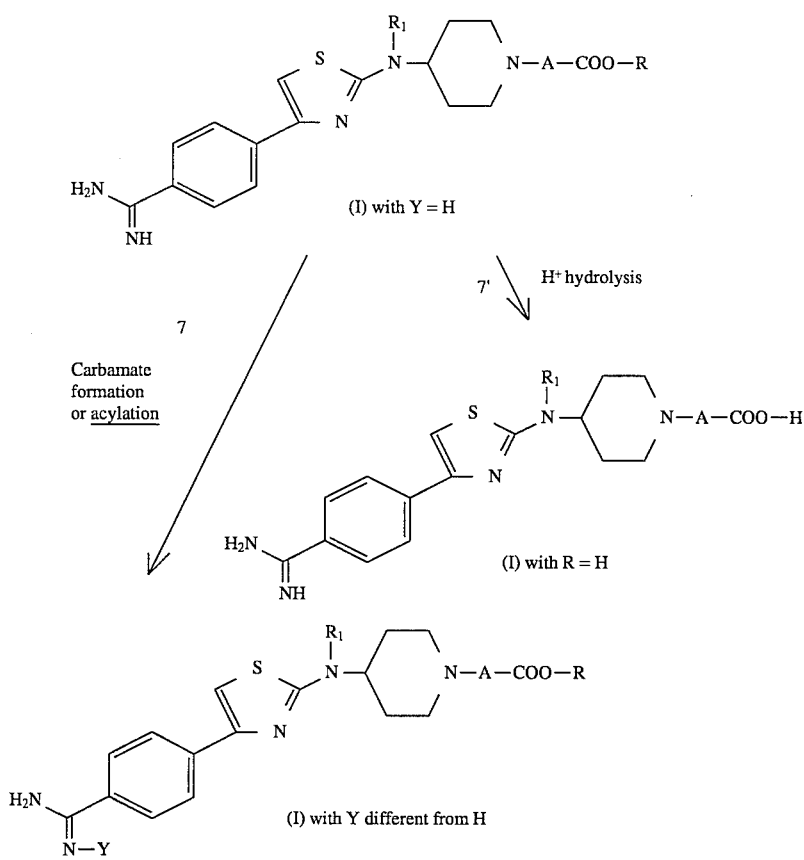

Given their antagonistic activity in relation to the binding of fibrinogen to the platelets, the compounds of the present invention are very useful in human and veterinary medicine, in particular for the treatment and prophylaxis of thrombotic disorders. Numerous examples of thrombotic disorders are known in the literature and comprise especially occlusive vascular diseases such as myocardial infarction, angina pectoris, transient ischaemic accidents, cerebral attacks of thrombotic origin, atherosclerosis, peripheral arterial diseases, nephropathies, retinopathies, post-operative thromboses, pulmonary embolies, veinous thromboses and in angioplasty.

The compounds according to the invention are also valuable and useful in the prophylaxis of peri- and post-operative complications consecutive to an organ, in particular a heart and kidney, transplant.

The compounds according to the invention are also useful for the treatment or the prophylaxis of other pathologies in which the GP IIb/IIIa complex or other receptors (integrin) are involved. Thus, for example, the compounds of the invention can be used to potentiate cicatrization, for the treatment of osteoporosis or of rheumatoid arthritis.

The compounds according to the invention can also be useful for the treatment of certain cancer diseases and are useful for preventing or stopping the development of cancerous metastases.

Another aspect of the invention relates to the pharmaceutically acceptable salts of the compounds according to the invention for their use in the treatment or the prophylaxis of thrombotic disorders, as well as the preparation of a medicinal product containing them.

The compounds according to the invention have been the subject of biochemical and pharmacological tests.

The pharmacological activity of the compounds (I) according to the invention was evaluated by platelet aggregation tests. These tests were carried out on samples obtained from man, baboons, dogs, guinea pigs, rabbits, rats and mice and made it possible to determine the in vitro activity of the compounds. The ex vivo activity of these products, administered via the intravenous or oral route, was also measured in baboons by the same method.

Platelet aggregation was induced according to one of the following two procedures:

Platelet aggregation procedure by turbidimetry according to G.V. Born, Aggregation of blood platelets by adenosine diphosphate and its reversal, Nature, 1962, 194, 927–929 modified according to SAVI et al., Nouv. Rev. Fr. Hematol, 1993, 35, 115–119.

Platelet aggregation (humans, dogs, guinea pigs, rabbits, rats, mice and baboons) was measured by turbidimetry on 400 µl of platelet-rich plasma (PRP) obtained by centrifugation from whole blood collected over a 3.8% trisodium citrate solution (9 vol/1 vol). 400 µl of PRP are deposited in the cell of an aggregometer, with stirring (900 revolutions/min), at 37° C. The aggregation is induced by the addition of 4 µl of a solution of aggregating agent.

Procedure for aggregation in whole blood according to Diodati et al., Circulation, 1992, 86, 1186–1193.

The platelet aggregation (dogs) is measured impedance on whole blood, collected over a hirudin solution at 100 µ/ml (9 vol/1 vol). 0.5 ml of whole blood thus collected and 0.5 ml of a 0.9% NaCl solution are deposited in the cell of the aggregometer, with stirring, at 37° C. and then the electrode is dipped in the cell. The aggregation is measured after activation with 10 μl of a solution of aggregating agent.

The aggregating agents studied were ADP (2.5 or 6.25 μM), arachidonic acid (500 μM), collagen (12.5 μg/ml), thrombin (0.1 μIU/ml) or PAF (0.5 μM). In the case of the in vitro tests, 10 μl of a 10% DMSO solution containing the compounds of the invention were introduced into the cell 30 seconds before the initiation of the aggregation. The controls were carried out in the presence of the same volume of solvent.

The compounds according to the invention exhibit activity in relation to platelet aggregation at a concentration of between 1 nM and 10 μM and regardless of the aggregating agent used.

After oral or intravenous administration, a pharmacological activity could be observed in baboons for some compounds administered via the intravenous or oral route, at doses ranging from 0.01 to 100 mg/kg.

The compounds of formula (I) are not very toxic; their toxicity is compatible with their use as medicinal product for the treatment of the disorders and diseases above.

The compounds of formula (I) can be formulated in pharmaceutical compositions for administration to mammals, including man, for the treatment of the abovementioned diseases.

The above compounds of formula (I) and their pharmaceutically acceptable salts can be used at daily doses of 0.01 to 100 mg per kilogram of body weight of the mammal to be treated, preferably at daily doses of 0.01 to 5 mg/kg.

In human beings, the dose may range preferably from 0.1 to 500 mg per day, more particularly from 2 to 500 mg depending on the age of the subject to be treated or the type of treatment: prophylactic or curative.

In the pharmaceutical compositions of the present invention, the active ingredient is generally formulated in dosage units containing from 0.01 to 500 mg, advantageously from 0.2 to 500 mg, preferably from 0.2 to 200 mg of the said active ingredient per dosage unit.

The subject of the present invention is therefore also the pharmaceutical compositions which contain, as active ingredient, one of the above compounds. These compositions are produced so as to be able to be administered via the oral or parenteral route.

In the pharmaceutical compositions of the present invention for oral, sublingual, subcutaneous, intramuscular, intravenous, transdermal, local or rectal administration, the active ingredient may be administered in unit forms for administration, mixed with conventional pharmaceutical carriers, to animals and to human beings. The appropriate unit forms for administration comprise the oral forms such as tablets, gelatin capsules, powders, granules and oral solutions or suspensions, the forms for sublingual and buccal administration, the forms for subcutaneous, intramuscular, intravenous, intranasal or intraocular administration and the forms for rectal administration.

When a solid composition is prepared in the form of tablets, the principal active ingredient is mixed with a pharmaceutical vehicle such as gelatin, starch, lactose, magnesium stearate, talc, gum arabic and the like. The tablets may be coated with sucrose or with other appropriate materials or alternatively they can be treated such that they have a prolonged or delayed activity and release continuously a predetermined quantity of active ingredient.

The preparation in gelatin capsules is obtained by mixing the active ingredient with a diluent and by pouring the mixture obtained into soft or hard gelatin capsules.

A preparation in syrup or elixir form may contain the active ingredient together with a sweetener, preferably calorie-free, methylparaben and propylparaben as antiseptic, as well as a taste-enhancing agent and an appropriate colouring.

The water-dispersible powders or granules may contain the active ingredient mixed with dispersing agents or wetting agents, or suspending agents, such as polyvinylpyrrolidone, as well as with sweeteners or flavour correctors.

For rectal administration, suppositories are used which are prepared with binders which melt at the rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersing agents and/or wetting agents, for example propylene glycol or butylene glycol.

The active ingredient can also be formulated in the form of microcapsules, optionally with one or more carriers or additives.

The active ingredient can also be presented in the form of a complex with a cyclodextrin, for example α-, β- or γ-cyclodextrin, 2-hydroxypropyl-β-cyclodextrin or methyl-β-cyclodextrin.

The following PREPARATIONS and EXAMPLES illustrate the invention without however limiting it.

Preparation of the intermediates of formulae (II), (III) and (IV)

PREPARATION I

N-(1-Benzylpiperid-4-yl)-N'-tert-butylthiourea- (Compound 1)

24.93 g of 4-amino-1-benzylpiperidine are dissolved in 300 ml of dichloromethane and then 16.7 ml of tert-butylisothiocyanate are added dropwise and at room temperature. The reaction mixture is stirred at room temperature for 5 hours and then water is added and the mixture is allowed to settle. The organic phase is separated, dried over sodium sulphate and evaporated. The residue obtained is crystallized from petroleum ether in order to give white crystals which melt at 137° C.; yield: 88%.

PREPARATION II

N-(1-Benzylpiperid-4-yl)thiourea hydrobromide (Compound 2)

17 g of N-(1-benzylpiperid-4-yl)-N'-tert-butylthiourea are added to 170 ml of 33% hydrobromic acid in acetic acid; the reaction mixture is stirred at room temperature for 4 hours, then it is poured over diethylether. The crystals obtained are filtered and they are thoroughly washed with diethylether in order to obtain white crystals which melt at 120° C.; yield: quantitative.

PREPARATION III

4-{2-[N-(1-Benzylpiperid-4-yl)amino]-1,3-thiazol-4-yl}benzonitrile dihydrobromide (Compound 3, (II) with $R_1$=H)

12.46 g of 4-cyanophenacyl bromide are added to 18.38 g of N-(1-benzylpiperid-4-yl)thiourea hydrobromide in 200 ml of methanol, and then the reaction mixture is heated under reflux for 4 hours. The mixture is cooled to room temperature and then, successively, 200 ml of diethyl ether are added and the precipitate is filtered and washed with diethyl ether in order to obtain white crystals which melt at 280° C.; yield: 86%.

PREPARATION IV

4-{2-[N-(1-Benzylpiperid-4-yl)-N-methylamino]-1,3-thiazol-4-yl}benzonitrile (Compound 4.1, (II) with $R_1$=$CH_3$)

1.3 g of 4-{2-[N-(1-benzylpiperid-4-yl)amino]-1,3-thiazol-4-yl}benzonitrile dissolved in 5 ml of N,N-dimethylformamide are added, at room temperature, to 146 mg of sodium hydride (at 60% in dispersion in oil) in suspension in 13 ml of N,N-dimethylformamide and the reaction mixture is stirred for 15 minutes at this temperature. 0.23 ml of methyl iodide is then added, the reaction mixture is stirred for 4 hours at room temperature, and it is poured over water and extracted with ethyl acetate. The organic phase is washed with water, dried over sodium sulphate and evaporated. The residue is purified by silica gel chromatography, eluting with dichloromethane. Yellow crystals are obtained which melt at 136° C.; yield: 67%.

Ethyl 3-{N-(1-benzylpiperid-4-yl)-N-[4-(4-cyano-phenyl)-1,3-thiazol-2-yl]amino}propionate oxalate (Compound 4.2, (II) with $_1$=$-CH_2-CH_2-COOC_2H_5$)

25.92 ml of ethyl acrylate, 32.98 g of potassium carbonate and 7.7 g of tetrabutylammonium bromide are added to 44.8 g of 4-{2-[N-(1-benzylpiperid-4-yl)amino]-1,3-thiazol-4-yl}benzonitrile in 900 ml of toluene, and then the reaction mixture is heated under reflux for 24 hours. The reaction mixture is cooled, then water is added and the mixture is separated after settling has taken place. The organic phase is dried over sodium sulphate and then evaporated to dryness. The oil obtained is taken up in isopropyl ether and filtered on a silica bed, entraining with isopropyl ether. The evaporation of the filtrate leads to a resin which is then salified by addition of one equivalent of oxalic acid in acetone in order to provide white crystals which melt at 225° C.; yield 84%.

PREPARATION V

4-{2-[N-(piperid-4-yl)amino]-1,3-thiazol-4-yl }-benzonitrile dihydrochloride (Compound 5.1, (III) with $R_1$=H)

This compound is obtained by the action of chloroformares as described in Tetrahedron Letters, 1983, 24, 31, 3233–3236 and more particularly by the action of 1-chloroethyl chloroformate according to J. Org. Chem., 1984, 49, 2081–2082.

6.2 g of 1,8-bis-dimethylaminonaphthalene are added to 18 g of 4-{2-[N-(1-benzylpiperid-4-yl)amino]-1,3-thiazol-4-yl}benzonitrile in 250 ml of 1,2-dichloroethane and then the reaction mixture is cooled to 0° C., 10.4 ml of 1-chloroethyl chloroformate are added and then the reaction mixture is stirred for 30 minutes at this temperature and then heated under reflux for 3 hours. The mixture is evaporated to dryness and the residue is taken up in 250 ml of methanol and then the mixture is heated under reflux for 2 hours. The reaction mixture is allowed to cool and then, successively, 250 ml of diethyl ether are added, the mixture is filtered, washed with diethyl ether and dried in order to obtain beige crystals which melt at 266° C.; yield 87%.

4-{2-[N-(piperid-4-yl)-N-methylamino]-1,3-thiazol-4-yl}benzonitrile dihydrochloride (Compound 5.2, (III) with $R_1$=$CH_3$)

This compound is obtained according to the same procedure as for Compound 5.1, by debenzylation of 4-{2-[N-(1-benzylpiperid-4-yl)-N-methylamino]-1,3-thiazol-4-yl}benzonitrile. Beige crystals are obtained which melt at 175° C.; yield 67%.

Ethyl 3-{N-[4-(4-cyanophenyl)-1,3-thiazol-2-yl]-N-(piperid-4-yl)amino}propionate dihydrochloride (Compound 5.3, (III) with $R_1$=$-CH_2-CH_2-COOC_2H_5$)

This compound is obtained according to the same procedure as for Compound 5.1 by debenzylation of ethyl 3-{N-(1-benzylpiperid-4-yl)-N-[4-(4-cyanophenyl)-1,3thiazol-2-yl]amino}propionate. White crystals are obtained which melt at 140° C.; yield 70%.

PREPARATION VI

Methyl {4-[4-(4-cyanophenyl)-1,3-thiazol-2-ylamino]piperid-1-yl}acetate (Compound 6.1, (IV) with $R_1$=H, A=$CH_2$ and R=$CH_3$)

17.75 g of potassium carbonate and 4.3 ml of methylbromoacetate are added to 14.8 g of 4-{2-[(piperid-4-yl) amino]-1,3-thiazol-4-yl}benzonitrile dihydrochloride in 150 ml of N,N-dimethylformamide and the reaction mixture is heated at 50° C. for 2 hours. It is poured over water, extracted with ethyl acetate and the organic phase is washed with water, and then dried over sodium sulphate and concentrated under vacuum. The residue crystallizes from isopropyl ether to give beige crystals which melt at 172° C.; yield 86%.

Ethyl 3-{N-[4-(4-cyanophenyl)-1,3-thiazol-2-yl]-N-(1-ethoxycarbonylmethylpiperid-4-yl)amino}propionate (Compound 6.2, (IV) with $R_1$=$-C_2-C_2-COOC_2H_5$, A=$C_2$ and R=$C_2H_5$)

This compound is obtained according to the same procedure as for Compound 6.1, by N-alkylation of ethyl 3-{N-[4-(4-cyanophenyl)-1,3-thiazol-2-yl]-N-(piperid-4-yl)amino}propionate dihydrochloride with ethyl bromoacetate. A colourless resin is obtained; yield 85%.

$^1$H NMR (DMSO-$d_6$) δ: 1.16 (m, 6H); 1.73–1.96 (m, 4H); 2.29 (m, 2H); 2.66 (m, 2H); 2.89 (m, 2H); 3.23 (s, 2H); 3.50 (m, 1H); 3.62 (m, 2H); 4.04 (m, 4H); 7.49 (s, 1H); 7.82 (d, J=8.44 Hz, 2H); 7.98 (d, J=8.44 Hz, 2H).

PREPARATION VII

Methyl 3-{4-[4-(4-cyanophenyl)-1,3-thiazol-2-yl-amino]piperid-1-yl}propionate (Compound 7.1)

This compound is obtained by Michael reaction with an α, β-unsaturated ester in an alkanol, according to Organic Reaction, 1967, Vol. 10, 173.

1.64 ml of triethylamine are added to 2 g of 4-{2-[(piperid-4-yl)amino]-1,3-thiazol-4-yl}benzonitrile in 30 ml of methanol, followed by 0.55 ml of methylacrylate and the reaction mixture is heated under reflux for 1 hour. The reaction mixture is then evaporated to dryness. The residue is purified by silica gel chromatography, eluting with a dichloromethane-methanol mixture (95/5). Concentration of the pure product fractions gives white crystals which melt at 154° C.; yield: 72%.

While carrying out the procedure according to PREPARATIONS VI and VII described above, Compounds 6.3 to 7.2, which are described in TABLE I below, are prepared:

This compound, as well as that of EXAMPLE 2 below, is obtained by the Pinner reaction according to Organic Functional Group Preparation, Sandler S. and Karo W., 1989, 12, III, Second Edition.

TABLE 1

(IV) Structure: 4-cyanophenyl-thiazole with N-R$_1$ and piperidine-N-A-COO-R substituent

| Compound | R$_1$ | −A−COO−R | mp.; °C., salt |
|---|---|---|---|
| 6.3 | H | −CH(COOCH$_3$)−COOCH$_3$ | 203 |
| 6.4 | H | −CH(COOCH$_3$)−(2-Cl-phenyl) | 200, 2HCl |
| 6.5 | −CH$_3$ | −CH$_2$−COOCH$_3$ | 107 |
| 6.6 | H | −CH$_2$−COOt-Bu | 50 |
| 6.7 | H | −CH$_2$−COOC$_2$H$_5$ | 153 |
| 6.8 | H | −CH(CH$_3$)−COOC$_2$H$_5$ | 113 |
| 6.9 | H | −C(CH$_3$)$_2$−COOC$_2$H$_5$ | 134 |
| 6.10 | H | −CH(COOCH$_3$)−phenyl | 78 |
| 6.11 | −CH$_2$−phenyl | −CH$_2$−COOCH$_3$ | 138 |
| 6.12 | −CH$_2$−COOC$_2$H$_5$ | −CH$_2$−COOCH$_3$ | Resin |
| 6.13 | −CH$_2$−COOCH$_3$ | −CH$_2$−COOCH$_3$ | 93 |
| 6.14 | −(CH$_2$)$_3$−COOC$_2$H$_5$ | −CH$_2$−COOC$_2$H$_5$ | 110; 2HCl |
| 6.15 | −CH$_2$−(4-COOCH$_3$-phenyl) | −CH$_2$−COOCH$_3$ | 110; 2HCl |
| 6.16 | −(CH$_2$)$_2$−COOCH$_3$ | −CH$_2$−COOCH$_3$ | Resin |
| 7.2 | H | −CH(COOCH$_3$)−CH$_2$−COOCH$_3$ | 134 |

EXAMPLE 1

Methyl (4-{4-[4-(aminoiminomethyl)phenyl]-1,3-thiazol-2-ylamino}piperid-1-yl)acetate hydrochloride (I) : Y=H;—A—COOR=—CH$_2$COOCH$_3$; R$_1$=H 10.33 g of methyl {4-[4-(4-cyanophenyl)-1,3-thiazol-2-ylamino}piperid-1-yl]acetate (Compound 6.1) are added to 150 ml of methanol saturated with hydrogen chloride at a temperature close to 0° C. and the reaction mixture is left at 4° C. overnight. The mixture is evaporated to dryness without heating and then the residue is taken up in 150 ml of methanol and ammonia is bubbled through until a basic pH is obtained. The reaction mixture is then heated under reflux for 2 hours and then it is evaporated to dryness and the residue obtained is purified by chromatography on a silica gel column, eluting with a dichloromethane-methanol mixture (8/2 - v/v). Concentration of the pure product fraction gives yellow crystals which melt at 150° C.; yield: 69%.

EXAMPLE 2

Ethyl 3-[N-{4-[4-(aminoiminomethyl)phenyl]-1,3thiazol-2-yl}-N-(1-ethoxycarbonylmethylpiperid-4-yl)amino]propionate hydrochloride.

(I) : Y=H; —A—COOR=—CH$_2$—COOC$_2$—H$_5$; R$_1$=—CH$_2$—CH$_2$—COOC$_2$H$_5$

A solution of 1.25 g of ethyl 3-{N-[4-(4-cyano-phenyl)-1,3-thiazol-2-yl]-N-(1-ethoxycarbonylmethyl -piperid-4-yl)amino}propionate (Compound 6.2) in 25 ml of ethanol is saturated at 0° C. with hydrogen chloride; the reaction mixture is left at 4° C. overnight and then it is evaporated to dryness without heating and, successively, the residue is taken up in 40 ml of ethanol and a stream of ammonia is bubbled through until a basic pH is obtained. The reaction mixture is then heated under reflux for 2 hours, is evaporated to dryness and the residue obtained is purified by chromatography on a silica gel column, eluting with a dichloromethanemethanol mixture (8/2 - v/v). Concentration of the pure product fraction gives yellow crystals which melt at 156° C.; yield: 76%.

By carrying out the procedure according to EXAMPLES 1 and 2 above, EXAMPLES 3 to 17, described in TABLE II below, are prepared.

TABLE II

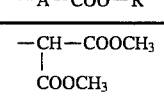

(I)

| Example | R$_1$ | —A—COO—R | m.p.; °C., salt |
|---|---|---|---|
| 3 | H | 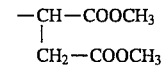 | 80, HCl |
| 4 | H | 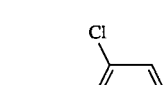 | 128, HCl |
| 5 | H | —CH$_2$—CH$_2$—COOCH$_3$ | 110, HCl |
| 6 | H | 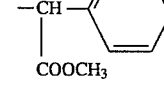 | 180, HCl |
| 7 | —CH$_3$ | —CH$_2$—COOCH$_3$ | 239, HCl |
| 8 | H | 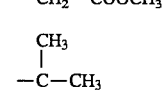 | 167, HCl |
| 9 | H | 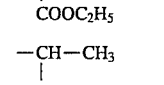 | 150, HCl |
| 10 | H | —CH$_2$—COOC$_2$H$_5$ | 140, HCl |
| 11 | H | 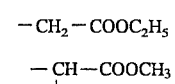 | 169, HCl |

TABLE II-continued

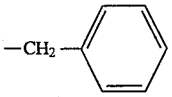

| Example | R₁ | —A—COO—R | m.p.; °C., salt |
|---|---|---|---|
| 12 | —CH₂—C₆H₅ | —CH₂—COOCH₃ | 190, HCl |
| 13 | —CH₂—COOC₂H₅ | —CH₂—COOCH₃ | 229, HCl |
| 14 | —CH₂—COOCH₃ | —CH₂—COOCH₃ | 247, HCl |
| 15 | —(CH₂)₃—COOC₂H₅ | —CH₂—COOC₂H₅ | 120, HCl |
| 16 | —CH₂—C₆H₄—COOCH₃ | —CH₂—COOCH₃ | 175, HCl |
| 17 | —(CH₂)₂—COOCH₃ | —CH₂—COOCH₃ | 233, HCl |

EXAMPLE 18

(4-{4-[4-(aminoiminomethyl)phenyl]-1,3-thiazol-2-ylamino}piperid-1-yl)acetic acid trihydrochloride (I) : Y=H; —A—COO—R=—CH₂COOH; R₁=H 1 g of methyl (4-{4-[4-(aminoiminomethyl)phenyl]-1,3-thiazol-2-ylamino}piperid-1-yl)acetate hydrochloride (EXAMPLE 1) is added to 20 ml of 6N hydrochloric acid and the reaction mixture is heated under reflux for 5 hours. The mixture is evaporated to dryness and the residue is crystallized from acetone to give white crystals which melt at 216° C.; yield: 96%.

EXAMPLE 19

3-[N-{4-[4-(aminoiminomethyl)phenyl]-1,3-thiazol-2-yl}-N-(1-carboxymethylpiperid-4-yl)amino]propionic acid trihydrochloride (I) : Y=H; —A—COO—R=—CH₂COOH; R₁=—CH₂—CH₂—COOH 700 mg of ethyl 3-[N-{4-[4-(aminoiminomethyl)phenyl]-1,3-thiazol-2-yl}-N-(1-ethoxycarbonylmethyl-piperid-4-yl)amino]propionate hydrochloride (EXAMPLE 2) are added to 25 ml of 6N hydrochloric acid and the reaction mixture is heated under reflux for 5 hours. The mixture is evaporated to dryness and the residue is crystallized from acetone to give white crystals which melt at 215° C.; yield: 80%.

By carrying out the procedure according to EXAMPLES 18 and 19 above, EXAMPLES 20 to 30, described in TABLE III below, are prepared.

TABLE III

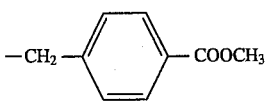

| Example | R₁ | —A—COO—R | m.p.; °C., salt |
|---|---|---|---|
| 20 | H | —CH(CH₂—COOH)—COOH | 105, 3HCl |

TABLE III-continued

Structure (I):

A thiazole compound with formula showing H₂N-C(=NH)- attached to phenyl, connected to thiazole, with N-C(=N)(R₁)-N linked to piperidine bearing N-A-COO-R substituent.

| Example | R₁ | —A—COO—R | m.p.; °C., salt |
|---|---|---|---|
| 21 | H | —CH(COOH)-(2-chlorophenyl) | 244, 3HCl |
| 22 | —CH₃ | —CH₂—COOH | 226, 3HCl |
| 23 | H | —CH₂—CH₂—COOH | 230, 3HCl |
| 24 | H | —CH(CH₃)—COOH | 226, 3HCl |
| 25 | H | —C(CH₃)₂—COOH | 256, 3HCl |
| 26 | H | —CH(phenyl)—COOH | 250, 3HCl |
| 27 | —CH₂-phenyl | —CH₂—COOH | 245, 3HCl |
| 28 | —CH₂—COOH | —CH₂—COOH | 220, 3HCl |
| 29 | —CH₂-(4-COOCH₃-phenyl) | —CH₂—COOH | 295, 3HCl |
| 30 | —(CH₂)₃—COOH | —CH₂—COOH | 100, 3HCl |

EXAMPLE 31

Methyl (4-{4-[4-(aminoethoxycarbonyliminomethyl)-phenyl]-1,3-thiazol-2-ylamino}piperid-1-yl)acetate (I) : Y=—COOCH₂CH₃; —A—COO—R=—CH₂COOCH₃; R₁=H 0.25 ml of ethyl chloroformate is added dropwise, while the temperature of the mixture is maintained at 0° C., to 1 g of methyl (4-{4-[4-(aminoiminomethyl)phenyl]-1,3-thiazol-2-ylamino}piperid-1-yl) acetate (EXAMPLE 1) in 20 ml of N,N-dimethylformamide in the presence of 0.71 ml of triethylamine, and then the reaction mixture is left for 15 minutes at this temperature and it is then stirred for 3 hours at room temperature. The reaction mixture is poured over water and, successively, it is extracted with ethyl acetate, the organic phase is washed with water, dried over sodium sulphate and evaporated to dryness. The residue crystallizes from isopropyl ether to give white crystals which melt at 194° C.; yield 76%.

EXAMPLE 32

Ethyl 3-[N-{4-[4-(amino(N-ethoxycarbonylimino)methyl)phenyl]-1,3-thiazol-2-yl}-N-(1-ethoxycarbonyl-methylpiperid-4-yl)amino]propionate (I) : Y=—COOC₂H₅; —A—COO—R=—CH₂COOC₂H₅; R₁=—CH₂—CH₂—COOC₂H₅

0.29 ml of ethyl chloroformate is added dropwise, while the temperature of the mixture is maintained at 0° C., to 1.5 g of ethyl 3-[N-{4-[4-(aminoiminomethyl)-phenyl]-1,3-thiazol-2-yl}-N-(1-ethoxycarbonylmethyl-piperid-4-yl)amino]propionate hydrochloride (EXAMPLE 2) in 20 ml of N,N-dimethylformamide in the presence of 0.84 ml of triethylamine. The reaction mixture is left for 15 minutes at this temperature and then it is stirred for 3 hours at room temperature. The reaction mixture is poured over water and then, successively, is extracted with ethyl acetate, the organic phase is washed with water, dried over sodium sulphate and evaporated to dryness. The residue crystallizes from isopropyl ether to leave white crystals which melt at 130° C.; yield 78%.

By carrying out the procedure according to EXAMPLES 31 and 32 above, EXAMPLES 33 to 41, described in TABLE III below, are prepared by reacting the derivatives described in TABLE II with the appropriate chloroformares of formula $C_1$—COO—$R_2$.

TABLE IV

[Structure: thiazole with H2N-C(=N-Y)- on phenyl, connected to piperidine N-A-COO-R with R1 on N]

| Example | Y | $R_1$ | —A—COO—R | m.p.; °C. |
|---|---|---|---|---|
| 33 | —COOCH$_3$ | H | —CH$_2$—COOCH$_3$ | 203 |
| 34 | —COOC$_2$H$_5$ | H | —CH$_2$—COOC$_2$H$_5$ | 189 |
| 35 | —COOCH$_3$ | H | —CH(COOCH$_3$)—COOCH$_3$ | 204 |
| 36 | —COOC$_2$H$_5$ | H | —CH(CH$_3$)—COOC$_2$H$_5$ | 108 |
| 37 | —COOC$_2$H$_5$ | H | —C(CH$_3$)$_2$—COOC$_2$H$_5$ | 124 |
| 38 | —COOC$_2$H$_5$ | H | —CH(C$_6$H$_5$)—COOCH$_3$ | 182 |
| 39 | —COOC$_2$H$_5$ | —(CH$_2$)$_2$—COOCH$_3$ | —CH$_2$—COOCH$_3$ | 133 |
| 40 | —COOCH$_3$ | —(CH$_2$)$_2$—COOC$_2$H$_5$ | —CH$_2$—COOC$_2$H$_5$ | 115 |
| 41 | —COOCH$_3$ | —(CH$_2$)$_2$—COOCH$_3$ | —CH$_2$—COOCH$_3$ | 134 |

We claim:

1. A compound of formula:

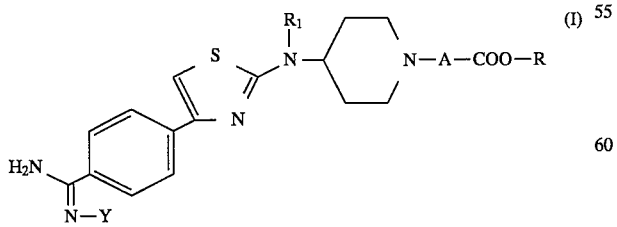

(I)

in which $R_1$ is selected from the group consisting of hydrogen, $C_1$–$C_5$ alkyl, $C_3$–$C_8$ cycloalkyl, aralkyl whose alkyl part has from 1 to 5 carbon atoms, alkoxycarbonylalkyl in which the alkoxy and alkyl parts have from 1 to 3 carbon atoms. (alkoxycarbonylaryl)-alkyl in which the alkoxy and alkyl parts have from 1 to 3 carbon atoms; carboxy-($C_1$–$C_3$)alkyl and (carboxyaryl)alkyl in which the alkyl part has from 1 to 3 carbon atoms;

A is selected from the group consisting of (i) methylene mono-substituted methylene, disubstituted methylene and (ii) ethylene;

R is selected from the group consisting of hydrogen, $C_1$–$C_5$ alkyl, aryl, aralkyl whose alkyl part has from 1 to 5 carbon atoms, substituted aryl and substituted aralkyl (in which the substituent, which is linked to the aromatic ring, is selected from the group consisting of hydroxyl, $C_1$–$C_3$ alkoxy, $C_1$–$C_3$ alkanoyloxy, halogen, trifluoromethyl and $C_1$–$C_5$ alkyl);

Y is selected from the group consisting of hydrogen; a —COOR$_2$ group in which R$_2$ is selected from the group consisting of $C_1$–$C_5$ alkyl, aryl, aralkyl whose alkyl part has from 1 to 5 carbon atoms, substituted aryl and substituted aralkyl whose alkyl part has from 1 to 5 carbon atoms (in which the substituent, which is linked to the aromatic ring, is $C_1$–$C_5$ alkyl); and a —COR$_3$ group in which R$_3$ represents $C_1$–$C_5$ alkyl;

or one of its salts.

2. A compound according to claim 1, in which Y represents hydrogen, —A— is selected from the group consisting of methylene and monosubstituted methylene and $R_1$ is selected from the group consisting of hydrogen, methyl, carboxyalkyl and alkoxycarbonylalkyl, or one of its salts.

3. A compound according to claim 1, in which Y represents a group —COOR$_2$ and —A— is selected from the group consisting of methylene and monosubstituted methylene in which R$_2$ is as defined for (I), or one of its salts.

4. A compound according to claim 1, in which —A— represents a group —CH$_2$—, or one of its salts.

5. A compound according to claim 1, in which $R_1$ is selected from the group consisting of hydrogen, carboxyalkyl and alkoxycarbonylalkyl, R is selected from the group consisting of hydrogen, methyl and ethyl or one of its salts.

6. A compound according to claim 1, in which R is selected from the group consisting of methyl and ethyl.

7. A compound according to claim 1 which is selected from the group consisting of:

a) methyl (4-{4-[4-(aminoiminomethyl)phenyl]-1,3-thiazol-2-ylamino}piperid-1-yl)acetate, b) (4-{4-[4-(aminoiminomethyl)phenyl]-1,3-thiazol-2-ylamino}piperid-1-yl}acetic acid, c) methyl (4-{4-[4-(amino(N-ethoxycarbonylimino)methyl)-phenyl]-1,3-thiazol-2-ylamino}piperid-1-yl)acetate, d) ethyl (4-{4-[4-(aminoiminomethyl)phenyl]-1,3-thiazol-2-ylamino}-piperid-1-yl)acetate, e) ethyl (4-{4-[4-(amino(N-ethoxycarbonylimino)methyl)-phenyl]-1,3-thiazol-2-ylamino}piperid-1-yl)acetate, f) (4-{4-[4-(aminoiminomethyl)phenyl]-1,3-thiazol-2-yl-N-carboxymethylamino}piperid-1-yl)acetic acid, g) ethyl 3-[N-{4-[4-(aminoiminomethyl)phenyl]-1,3-thiazol-2-yl}-N-(1-ethoxycarbonylmethylpiperid-4-yl)-amino]propionate, h) 3-[N-{4-[4-(aminoiminomethyl)phenyl]-1,3-thiazol-2-yl}-N-(1-carboxymethylpiperid-4-yl)amino]propionic acid, and i) ethyl 3-[N-{4-[4-(amino(N-ethoxycarbonylimino)methyl)-phenyl]-1,3-thiazol-2-yl}-N-(1-ethoxycarbonylmethylpiperid-4-yl)amino]propionate, or one of their salts.

8. A compound according to claim 1, in which the compound of formula (I) is in the form of a salt which is selected from the group consisting of hydrochloride, hydrobromide, sulphate, acetate, hydrogen sulphate, dihydrogen phosphate, methanesulphonate, methyl sulphate, maleate, fumarate, sulphonate, 2-naphthalenesulphonate, glycolate, gluconate, citrate, isethionate, benzoate, salicylate, ascorbate, tartrate, succinate, lactate, glutarate, toluenesulphonate, ascorbate and the salt of an inorganic base.

9. Process for the preparation of a compound of formula (I), which comprises the steps consisting of:

(a) deprotecting the cyclic amine functional group of a compound of formula II:

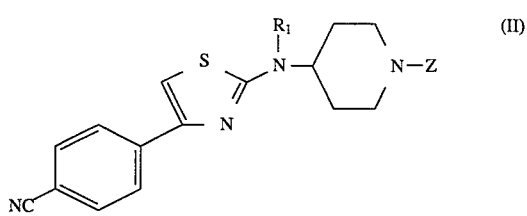

in which $R_1$ is as defined for (I) and Z represents an amine-protecting group, so as to obtain a free amine of formula:

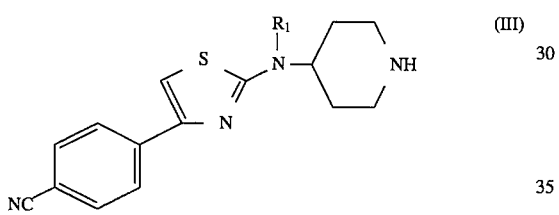

in which $R_1$ is as defined for (I):

(b) N-alkylating the resulting compound of formula (III)
  (i) either by a reaction with a halogenated derivative of formula:

in which X represents a leaving group, and A and R are as defined for (I), in a solvent which is selected from the group consisting of alkanols and dimethylformamide in the presence of an alkaline agent;
  (ii) or, by Michael reaction with an α, β-unsaturated ester of formula

or

in an alkanol where R is as defined for (I).
in order to obtain a compound of formula:

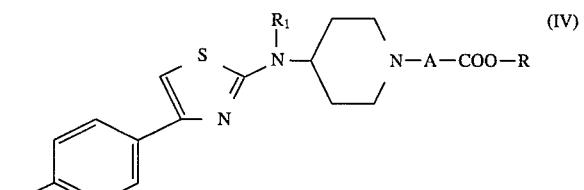

in which A, R and R, are as defined for (I), (c) subjecting the resulting compound to the Pinner reaction by reacting the nitrile (IV) in an acidic medium in an alkanol in order to obtain the imidate salt with which an amine, for example ammonia, is then reacted in order to obtain the amidine of formula:

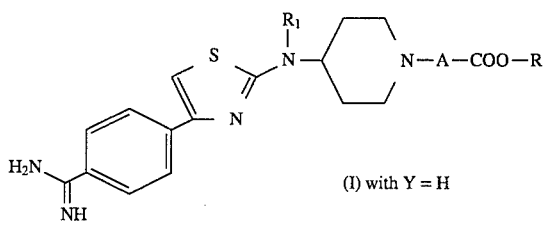

(I) with Y = H in which A, R and $R_1$ are as defined for (I), the compound obtained representing a compound of formula (I) in which Y is hydrogen, (d) where appropriate, reacting the amidine obtained in step (c),
  (i) either with a chloroformate of formula:

Cl—COO—$R_2$ in which $R_2$ is as defined for (I), in a solvent in an alkaline medium, in order to obtain the compound of formula:

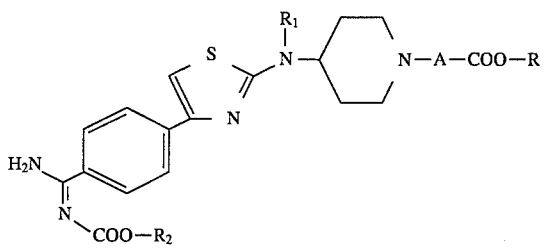

representing a compound of formula (I) in which Y represents —COO—$R_2$ and $R_1$, $R_2$, A and R are as defined for (I);
  (ii) or with an acylating agent such as Cl—CO—$R_3$ in which $R_3$ is as defined for (I) in order to obtain a compound of formula (I) in which Y represents 13 CO—$R_3$ or $R_1$, A and R being as defined for (I);

(e) where appropriate, hydrolysing the corresponding ester precursor obtained in step (c), for example in an acidic medium in the presence of hydrochloric acid, in order to obtain a compound of formula (I) in which R is hydrogen, or one of its salts.

10. A compound of formula:

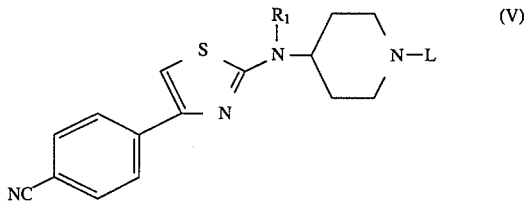

in which L is selected from the group consisting of hydrogen, an amino protecting group and a group —A—COOR, A, R and $_1$ being as defined for (I) in claim 1, or one of its salts.

11. A pharmaceutical composition which comprises a therapeutically effective dose of at least one compound according to claim 1 in combination with at least one pharmaceutical excipient.

12. A pharmaceutical composition in the form of dosage units comprising a therapeutically effective dose of at least one compound according to claim 1, in combination with at least one pharmaceutical excipient.

13. A pharmaceutical composition comprising from 0.01 to 500 mg of a compound according to claim 1 in combination with at least one excipient.

14. A compound selected from the compounds of formula:

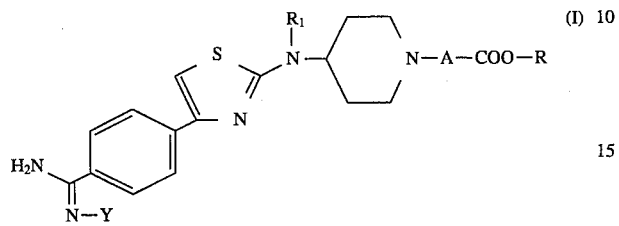

in which

R$_1$ is selected from the group consisting of hydrogen, C$_1$–C$_5$ alkyl, C$_3$–C$_8$ cycloalkyl, aralkyl whose alkyl part has from 1 to 5 carbon atoms, alkoxycarbonylalkyl in which the alkyl and alkoxy parts have from 1 to 3 carbon atoms and carboxyalkyl in which the alkyl part has from 1 to 3 carbon atoms;

A is selected from the group consisting of methylene, monosubstituted methylene, disubstituted methylene and ethylene;

R is selected from the group consisting of hydrogen, C$_1$–C$_5$ alkyl, aryl, substituted aryl, aralkyl and substituted aralkyl, in which alkyl part has from 1 to 5 carbon atoms, and the substituent is selected from hydroxy, C$_1$–C$_3$ alkoxy, halogen, trifluoromethyl and C$_1$–C$_5$ alkyl;

Y is selected from the group consisting of hydrogen; a —COOR$_2$ group in which R$_2$ is selected from C$_1$–C$_5$ alkyl, aryl, substituted aryl, aralkyl, substituted aralkyl in which alkyl part has from 1 to 5 carbon atoms and the substituent is selected from C$_1$–C$_5$ alkyl; and a —COR$_3$ group in which R$_3$ is C$_1$–C$_5$ alkyl;

or a salt thereof.

15. A compound according to claim 1, in the form of a racemic mixture, or one of its salts.

16. A compound according to claim 1, in the form of an enantiomer, or one of its salts.

* * * * *